US007666867B2

(12) United States Patent
Makriyannis et al.

(10) Patent No.: US 7,666,867 B2
(45) Date of Patent: Feb. 23, 2010

(54) HETEROINDANES: A NEW CLASS OF POTENT CANNABIMIMETIC LIGANDS

(75) Inventors: Alexandros Makriyannis, Watertown, MA (US); Qian Liu, Malden, MA (US); Alexander M Zvonok, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 14 days.

(21) Appl. No.: 10/493,093

(22) PCT Filed: Oct. 28, 2002

(86) PCT No.: PCT/US02/34395

§ 371 (c)(1),
(2), (4) Date: Jul. 2, 2004

(87) PCT Pub. No.: WO03/035005

PCT Pub. Date: May 1, 2003

(65) Prior Publication Data

US 2004/0236101 A1 Nov. 25, 2004

Related U.S. Application Data

(60) Provisional application No. 60/348,869, filed on Oct. 26, 2001.

(51) Int. Cl.
*A61K 31/535* (2006.01)
*C07D 231/56* (2006.01)

(52) U.S. Cl. .................... 514/231.5; 514/322; 514/397; 514/403; 548/362.5; 548/311.7; 544/116; 546/199

(58) Field of Classification Search .............. 548/362.5, 548/311.7; 544/116; 546/199; 514/231.5, 514/322, 397, 403
See application file for complete search history.

(56) References Cited

U.S. PATENT DOCUMENTS

| 3,041,343 | A | 6/1962 | Jucker et al. |
| 3,465,024 | A | 9/1969 | Brownstein et al. |
| 3,573,327 | A | 3/1971 | Miyano |
| 3,577,458 | A | 5/1971 | Brownstein et al. |
| 3,656,906 | A | 4/1972 | Bullock |
| 3,838,131 | A | 9/1974 | Gauthier |
| 3,886,184 | A | 5/1975 | Matsumoto et al. |
| 3,897,306 | A | 7/1975 | Vidic |
| 3,915,996 | A | 10/1975 | Wright |
| 3,928,598 | A | 12/1975 | Archer |
| 3,944,673 | A | 3/1976 | Archer |
| 3,946,029 | A | 3/1976 | Descamps et al. |
| 3,953,603 | A | 4/1976 | Archer |
| 4,036,857 | A | 7/1977 | Razdan et al. |
| 4,054,582 | A | 10/1977 | Blanchard et al. |
| 4,087,545 | A | 5/1978 | Archer et al. |
| 4,087,546 | A | 5/1978 | Archer et al. |
| 4,087,547 | A | 5/1978 | Archer et al. |
| 4,088,777 | A | 5/1978 | Archer et al. |
| 4,102,902 | A | 7/1978 | Archer et al. |
| 4,152,450 | A | 5/1979 | Day et al. |
| 4,171,315 | A | 10/1979 | Ryan |
| 4,176,233 | A | 11/1979 | Archer et al. |
| 4,179,517 | A | 12/1979 | Mechoulam |
| 4,188,495 | A | 2/1980 | Althuis et al. |
| 4,208,351 | A | 6/1980 | Archer et al. |
| 4,278,603 | A | 7/1981 | Thakkar et al. |
| 4,282,237 | A | 8/1981 | Silvestrini .................... 514/406 |
| 4,282,248 | A | 8/1981 | Mechoulam et al. |
| 4,382,943 | A | 5/1983 | Winter et al. |
| 4,395,560 | A | 7/1983 | Ryan |
| 4,497,827 | A | 2/1985 | Nelson |
| 4,550,214 | A | 10/1985 | Mehta |
| 4,758,597 | A | 7/1988 | Martin et al. |
| 4,812,457 | A | 3/1989 | Narumiya |
| 4,876,276 | A | 10/1989 | Mechoulam |
| 4,885,295 | A | 12/1989 | Bell et al. |
| 5,017,573 | A | 5/1991 | Kon et al. .................... 514/218 |
| 5,053,548 | A | 10/1991 | Tanaka et al. |
| 5,068,234 | A | 11/1991 | D'Ambra et al. |
| 5,147,876 | A | 9/1992 | Mizuchi et al. |
| 5,223,510 | A | 6/1993 | Gubin et al. |
| 5,272,154 | A | 12/1993 | Dixon et al. ................. 514/299 |

(Continued)

FOREIGN PATENT DOCUMENTS

CA     2160420     10/1995

(Continued)

OTHER PUBLICATIONS

Archer et al; "cannabinoids, synthesis approaches to 9-ketocannabinoids."; J. Org. Chem.; vol. 42; No. 13; 2277-2284; (1977).
Mechoulam et al; "Synthesis of the individual, pharmacologically distinct, enantiomers of a tetrahydrocannabinol derivative"; Tetrahedron Asymmetry; 1:315-318; (1990) (abstract only).
European Search Report for Application No. EP 02 78 9293 dated Dec. 7, 2004.
Lan, R. et al; "Structure-Activity Relationships of Pyrazole Derivatives as Cannabinoid Receptor Antagonists"; J. Med. Chem.; vol. 42(4); 769-776; (1999).
K. Kim et al.; "AM1241, a cannabinoid $CB_2$ receptor selective compound, delays disease progression in a mouse model of amyotrophic lateral sclerosis"; European Journal of Pharmacology 542 (2006) 100-105.

(Continued)

*Primary Examiner*—Rei-tsang Shiao
(74) *Attorney, Agent, or Firm*—Alix, Yale & Ristas, LLP

(57) ABSTRACT

One aspect of the invention is concerned with cannabimimetic heteroindane analogs having affinities and/or selectivities for a cannabinoid receptor. A further aspect of the invention is concerned with pharmaceutical preparations employing the inventive analogs and methods of administering therapeutically effective amounts of the inventive analogs to provide a physiological effect.

21 Claims, 3 Drawing Sheets

U.S. PATENT DOCUMENTS

| | | | |
|---|---|---|---|
| 5,278,183 A * | 1/1994 | Silvestrini | 514/403 |
| 5,284,867 A | 2/1994 | Kloog | |
| 5,324,737 A | 6/1994 | D'Ambra et al. | |
| 5,434,295 A | 7/1995 | Mechoulam et al. | |
| 5,440,052 A | 8/1995 | Makriyannis et al. | |
| 5,462,960 A | 10/1995 | Barth et al. | |
| 5,489,580 A | 2/1996 | Makriyannis et al. | |
| 5,521,215 A | 5/1996 | Mechoulam | |
| 5,532,237 A | 7/1996 | Gallant et al. | |
| 5,538,993 A | 7/1996 | Mechoulam | |
| 5,576,436 A | 11/1996 | McCabe et al. | |
| 5,605,906 A | 2/1997 | Lau | |
| 5,607,933 A | 3/1997 | D'Ambra et al. | |
| 5,618,955 A | 4/1997 | Mechoulam et al. | |
| 5,624,941 A | 4/1997 | Barth et al. | |
| 5,631,297 A | 5/1997 | Pate et al. | |
| 5,635,530 A | 6/1997 | Mechoulam | |
| 5,688,825 A | 11/1997 | Makriyannis et al. | |
| 5,744,459 A | 4/1998 | Makriyannis et al. | |
| 5,747,524 A | 5/1998 | Cullinan et al. | |
| 5,760,028 A * | 6/1998 | Jadhav et al. | 514/211.03 |
| 5,776,932 A | 7/1998 | Schindler et al. | 514/235.2 |
| 5,804,601 A | 9/1998 | Kato et al. | |
| 5,817,651 A | 10/1998 | D'Ambra et al. | |
| 5,872,148 A | 2/1999 | Makriyannis et al. | |
| 5,874,459 A | 2/1999 | Makriyannis et al. | |
| 5,925,628 A | 7/1999 | Lee et al. | |
| 5,925,768 A | 7/1999 | Barth et al. | |
| 5,932,610 A | 8/1999 | Shohami et al. | |
| 5,939,429 A | 8/1999 | Kunos et al. | |
| 5,948,777 A | 9/1999 | Bender et al. | |
| 6,013,648 A | 1/2000 | Rinaldi et al. | |
| 6,028,084 A | 2/2000 | Barth et al. | |
| 6,096,740 A | 8/2000 | Mechoulam | |
| 6,127,399 A | 10/2000 | Yuan | |
| 6,166,066 A | 12/2000 | Makriyannis et al. | |
| 6,284,788 B1 | 9/2001 | Mittendorf et al. | |
| 6,391,909 B1 | 5/2002 | Makriyannis et al. | |
| 6,579,900 B2 | 6/2003 | Makriyannis et al. | |
| 6,610,737 B1 | 8/2003 | Garzon et al. | |
| 6,864,291 B1 | 3/2005 | Fride et al. | |
| 6,897,231 B2 * | 5/2005 | Bhagwat et al. | 514/403 |
| 6,903,137 B2 | 6/2005 | Fride et al. | |
| 2002/0119972 A1 | 8/2002 | Leftheris et al. | |
| 2002/0173528 A1 | 11/2002 | Fride et al. | |
| 2003/0120094 A1 | 6/2003 | Makriyannis et al. | |
| 2003/0149082 A1 | 8/2003 | Makriyannis et al. | |
| 2004/0077649 A1 | 4/2004 | Makriyannis et al. | |
| 2004/0077851 A1 | 4/2004 | Makriyannis et al. | |
| 2004/0087590 A1 | 5/2004 | Makriyannis et al. | |
| 2004/0192667 A1 | 9/2004 | Makriyannis et al. | |
| 2004/0236116 A1 | 11/2004 | Makriyannis et al. | |

FOREIGN PATENT DOCUMENTS

| | | |
|---|---|---|
| CA | 2222532 | 5/1996 |
| CA | 2304826 | 9/1998 |
| CA | 2 070 573 | 4/2003 |
| EP | 0276732 | 8/1988 |
| EP | 0444451 | 9/1991 |
| EP | 0471609 | 6/1993 |
| EP | 0576357 | 12/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| WO | WO 93/13099 | 7/1993 |
| WO | WO 94/12466 | 6/1994 |
| WO | WO 97/00860 | 1/1997 |
| WO | WO 97/21682 | 6/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 * | 8/2001 |
| WO | WO 02/058636 | 8/2002 |
| WO | WO 03/020217 | 3/2003 |
| WO | WO 03/063758 | 8/2003 |
| WO | WO 03/064359 | 8/2003 |

OTHER PUBLICATIONS

Bujalska, M. "Effect of Cannabinoid Receptor Agonists on Streptozotocin-Induced Hyperalgesia in Diabetic Neuropathy". *Pharmacology.* 82, (3), 193-200, 2008.

Ibrahim, M. M., Deng, H., Zvonok, A., Cockayne, D. A., Kwan, J., Mata, H. P., Vanderah, T. W., Lai, J., Porreca, F., Makriyannis, A.; Malan, T. P., Jr. "Activation of CB2 cannabinoid receptors by AM1241 inhibits experimental neuropathic pain: Pain inhibition by receptors not present in the CNS". *Proc. Natl. Acad. Sci. U. S. A.* 100, (18), 10529-10533, 2003.

Shoemaker, J. L., Seely, K. A., Reed, R. L., Crow, J. P.; Prather, P. L. "The CB2 cannabinoid agonist AM-1241 prolongs survival in a transgenic mouse model of amyotrophic lateral sclerosis when initiated at symptom onset". *J. Neurochem.* 101, (1), 87-98, 2007.

Ashton, J. C.; Glass, M. "The Cannabinoid CB2 Receptor as a Target for Inflammation-Dependent Neurodegeneration". *Curr Neuropharmacol* 5, (2), 73-80, 2007.

Benito, C., Tolon, R. M., Pazos, M. R., Nunez, E., Castillo, A. I.; Romero, J. "Cannabinoid CB2 receptors in human brain inflammation". *Br J Pharmacol* 153, (2), 277-85, 2008.

Fernandez-Ruiz, J., Pazos, M. R., Garcia-Arencibia, M., Sagredo, O.; Ramos, J. A. "Role of CB2 receptors in neuroprotective effects of cannabinoids". *Mol Cell Endocrinol* 286, (1-2 Suppl 1), S91-6, 2008.

Marchalant, Y., Rosi, S.; Wenk, G. L. "Anti-inflammatory property of the cannabinoid agonist WIN-55212-2 in a rodent model of chronic brain inflammation". *Neuroscience* 144, (4), 1516-22, 2007.

U.S. Appl. No. 09/600,786, filed Nov. 24, 1999, Makriyannis et al.
U.S. Appl. No. 09/698,071, filed Oct. 30, 2000, Fride et al.
U.S. Appl. No. 09/701,989, filed Jun. 9, 1999, Makriyannis et al.
U.S. Appl. No. 10/110,865, filed Oct. 18, 2000, Makriyannis et al.
U.S. Appl. No. 10/110,830, filed Oct. 18, 2000, Makriyannis et al.
U.S. Appl. No. 10/110,812, filed Oct. 18, 2000, Makriyannis et al.
U.S. Appl. No. 10/110,862, filed Oct. 18, 2000, Makriyannis et al.
U.S. Appl. No. 10/111,059, filed Oct. 18, 2000, Makriyannis et al.
U.S. Appl. No. 10/647,544, filed Aug. 25, 2003, Makriyannis et al.
U.S. Appl. No. 10/899,191, filed Jul. 26, 2004, Makriyannis et al.

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; CODEN: JMCMAR; ISSN: 0022-2623; XP002040932.

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenated Dibenzo[b,d]pyran-6-ones Related to Ellagic Acid, J. Org. Chem. 1991, 56, 3763-3768.

Archer et al; "cannabinoids, synthesis approaches to 9-ketocannabinoids."; *J. Org. Chem.*; vol. 42; No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Barnett-Norris et al; "Exploration of biologically relevant conformations of anandamide, . . . "; J. Med. Chem.; vol. 41; 4861-4872; 1998.
Beak, P.; and Brown, R A., The Tertiary Amide as an Effective Director of Ortho Lithiation, J. Org. Chem. 1982, 47, 34-36.
Belgaonkar et al; "synthesius of isocoumarins"; Indian J. Chem; vol. 13; No. 4; 336-338; 1975 (abstract only).
Beltramo M., Stella N., Calignano A., Lin S. Y., Makriyannis A., Piomelli D; "Functional Role Of High-Affinity Anandamide Transport, as Revealed by Selective Inhibition"; Science; vol. 277; 1094-1097; 1997.
Beltramo M., Piomelli D; "Anandamide Transport Inhibition by the Vanilloide Agonist Olvanil"; Europeean J. of Pharmacology; (1999); 364(1); 75-78 (abstract only).
Berdyshev EV, Cannabinoid receptors and the regulation of immune response. Chem Phys Lipids. Nov. 2000; 108(1-2):169-90.
Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998).
Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).
Bracey, M et al, Structural Adaptations in a Membrane Enzyme That Terminates Endocannabinoid Signaling. Science 2002; 298(5599): 1793-1796.
Brenneisen R, Pgli A, Elsohly MA, Henn V. Spiess Y: The effect of orally and rectally administered Δ9—tetrahydrocannabinol on spasticity, a pilot study with 2 patients. Int. J. Clin Pharmacol Ther. (1996) 34:446-452. (abstract only).
Brotchie JM: Adjuncts to dopamine replacement a pragmatic approach to reducing the problem of dyskinesia in Parkinson's disease. Mov. Disord. (1998)13:871-876. (abstract only).
Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).
Buckley NE, McCoy KI, Mpzey E et al, "Immunomodulation by cannabinoids is absent in mice deficient for the cannabinoid CB2 receptor"; Eur. J Pharmacol (2000) 396:141-149.
Burstein et al; "detection of cannabinoid receptors . . . "; Biochem. Biophys. Res. Commun.; vol. 176(1); 492-497; 1991 (abstract only).
Busch-Peterson et al; "Unsaturated side chain beta-11-hydroxyhexahydrocannabinol analogs"; J. Med. Chem.; 39; 3790-3796; (1996).
Calignano A, La Rana G. Diuffrida A, Piomelli D; "Control of pain initiation by endogenous cannabinoids"; Nature (1998) 394:277-291. (abstract only).
Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.
Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.
Campbell FA et al; "Are cannabinoids an effective and safe treatment option in the management of pain? A qualitative systematic review"; BMJ. Jul. 7, 2001;323(7303):13-6.
Charalambous A. et al; "5'-azido Δ8-THC: A Novel Photoaffinity Label for the Cannabinoid Receptor"; J. Med. Chem., 35, 3076-3079 (1992).
Charalambous A. et al; "Pharmacological evaluation of halogenated . . . "; Pharmacol. Biochem. Behav.; vol. 40; No. 3; 509-512; 1991.
Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).
Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.
Cherest M., Lusinchi X.; "A novel electrophilic N-amidation via electron deficient complexes: action of ferric chloride on N-acetyloxyamides"; Tetrahedron Letters; 30(6); 715-718; 1989.
Colombo G, Agabio R, Diaz G. et al; "Appetite suppression and weight loss after the cannabinoid antagonist SR141716"; Life Sci. (1998) 63-PL13-PL117. (abstract only).
Compton D.R. et al; "Pharmacological Profile Of A Series Of Bicyclic Cannabinoid Analogs: Classification as Cannabimimetic Agents"; J. Pharmacol. Exp. Ther.; 260; 201-209; 1992. (abstract only).
Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.
Consroe P, Musty R, Rein J, Tillery W, Pertwee R; "The perceived effects of smoked cannabis on patents with multiple sclerosis"; Eur. Neurol. (1997) 38-44-48. (abstract only).
Coxon et al; "Derivatives of nopinone"; Aust. J. Chem.; 23; 1069-1071; (1970) (abstract only).
Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.
D'Ambra et al; "C-attached aminoalkylindoles: potent cannabinoid mimetics"; Bioorg. & Med. Chem. Lett., 1996, 6(1), 17-22.
D'Amour F.E. et al; "A Method for Determining Loss of Pain Sensation"; J. Pharmacol. Exp. Ther.; 72; 74-79; 1941.
Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.
DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.
Desarnaud F., Cadas H., Piomelli D.; "Anandamide amidohydrolase activity in rat brain microsomes"; J. Biol. Chem.; 270; 6030-6035; (1995).
Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.
Deutsch D.G., Chin S.A.; "Enzymatic synthesis and degradation of anandamide, a cannabinoid receptor agonist"; Biochemical Pharmacology; 46(5); 791-796; 1993.
Devane, W.A. et al; "Determination and Characterization of a Cannabinoid Receptor in a Rat Brain"; Mol. Pharmacol., 34, 605-613 (1988). (abstract only).
Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.
Di Marzo, V., Bisogno, T., Melck, D., Ross, R., Brockie, H., Stevenson, L., Pertwee, R., DePetrocellis, L., "Interactions between synthetic vanilloids and The endogenous cannabinoid system"; FEBS Letters; (1998); 437(3); 449-454. (abstract only).
Dodd, P.R. et al, A Rapid Method for Preparing Synaptosomes: Comparison with Alternative Procedures, Brain Res., 226, 107-118 (1981). (abstract only).
Dominiami et al; "Synthesis of 5-(tert-Alkyl)resorcinols"; J. Org. Chem. 42(2); 344-346; (1977).
Drake et al, "classical/nonclassical hybrid cannabinoids"; J. Med. Chem.; vol. 41(19); 3596-3608 (1998).
Edery et al; "Activity of novel aminocannabinoids in baboons"; J. Med. Chem.; 27; 1370-1373 (1984).
Eissenstat et al; "Aminoalkylindoles: structure-activity relationships of novel cannabinoid mimetics"; J. Med. Chem. 1995, vol. 38, No. 16, pp. 3094-3105; XP 000651090.
Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.
Fahrenholtz; "The synthesis of 2 metabolites of (-)-delta eight-tetrahydrocannabinol"; J. Org. Chem.; vol. 37(13); 1972; XP002111824.
Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

Fride, E. & Mechoulam, R.; "Pharmacological activity of the cannabinoid receptor agonist, anandamide, a brain constituent"; European Journal of Pharmacology, vol. 231; 313-314; 1993.

Galiegue S et al. ; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

Green K.; "Marijuana smoking vs. cannabinoids for glaucoma therapy."; Arch. Ophthamol. Nov. 1998 116(11); 1433-1437. (abstract only).

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

Hampson, A.J., Grimaldi M. Axpirod J. Wink D; "Cannabidiol and (-) Δ9 tetrahydrocannabinol are neuroprotective antioxidants"; Proc. Natl Acad Sci. USA (Jul. 1998) 95; 8268-8273.

Hanus et al; "Two new unsaturated fatty acid ethanolamides in brain that bind to the cannabinoid receptor"; Journal of medicinal Chemistry; 36(20); 3032-3034; 1993.

Hargreaves, K. et al; "A new sensitive method for measuring thermal nociception in cutaneous hyperalgesia"; Pain; 32; 77-88; (1988) (abstract only).

Hemming M, Yellowlees PM; "Effective treatment of Tourette's syndrome with marijuana" ; *J. Psychopharmacol*, (1993) 7:389-391.

Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydrocannabinols"; tetrahedron; vol. 51(4); 1017-1032; (1995).

Huffman et al; "Synthesis of 5',11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Jbilo, O., Derocq, J., Segui, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

Joy JE, Wagtson SJ, Benson JA; "Marijuana and Medicine Assessing the Science Base"; National Academy Press, Washington, DC, USA (1999). (abstract only).

Kaminski NE; "Regulation of the cAMP cascade, gene expression and immune function by cannabinoid receptors"; J Neuroimmunol. Mar. 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lang, W., Qin, C., Hill, W.A., Lin, S., Khanolkar, A.D., Makriyannis, A.; High-Performance Liquid Chromatographic Determination Of Anandamide Amidase Activity in Rat Brain Microsomes; Anal. Biochem; (1996), 238, 40-45 (abstract only).

Lang, W. et al; "Substrate Specificity and Stereoselectivity of Rat Brain Microsomal Anandamide Amidohydrolase"; J. Med. Chem.; vol. 42(5); 896-902; (1999).

Lavalle et al; "Efficient conversion of (1R, 5R)-(+)-alpha-pinene to (1S, 5R)-(-)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

Maccarron M., *Endocannabinoids and their actions. Vitamins and Hormones* 2002;65:225-255.

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

Markwell, M.A.K., S.M. Haas, L.L. Bieber, and N.E. Tolbert.; "A modification of the Lowry procedure to simplify protein determination in the membrane and lipoprotein samples." 1978; *Anal. Biochem.* 87:206-210.

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10- tetrahydro-6h-dibenzo[b,d]pyrans"; J. of Med. Chem.; vol. 20(1); 17-24; 1977; XP00211825.

Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; Structural Requirements for Binding of Anandamide Type Compounds to the Brain Cannabinoid Receptor; J. Med. Chem.; 1997; 40; 659-667.

Mechoulam et al; "Synthesis of the individual, pharmacologically distinct, enantiomers of a tetrahydrocannabinol derivative"; Tetrahedron Asymmetry; 1: 311-314; (1990) (abstract only).

Mechoulam et al; "Synthesis of the individual, pharmacologically distinct, enantiomers of a tetrahydrocannabinol derivative."; *Tetrahedron Asymmetry*; 1: 315-318; (1990).

Mechoulam, "Cannabinoids as therapeutic agents"; *CRC press*, 1986.

Mechoulam et al; "Towards Cannabinoid drugs—Revisited"; Progress in Medicinal Chemistry; 35; 199-243; Jul. 3, 1998.

Melck, D., Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284 (abstract only).

Meltzer et al; "An improved synthesis of cannabinol and cannabiorcol"; Synthesis; 1981:985 (1981).

Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

Melvin et al; "Structure-activity relationships for cannabinoid receptor-binding and analgesic activity: studies of bicyclic cannabinoid analogs"; Mol. Pharmacol.; 44(5); 1008-1015 (1993) (abstract only).

Merck Index; 11th edition; "Tetrahydrocannabinols" compound No. 9142; 1989.

Meschler, J. P., Kraichely, D. M., Wilken, G. H., Howlett, A. C.; "Inverse Agonist Properties of N-(Piperidin-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor"; Biochemical Pharmacology; (2000); vol. 60; No. 9; 1315-1322.

Morgan Dr: *Therapeutic Uses of Cannabis. Harwood Academic Publishers, Amsterdam.* (1997).

Morris, S,; Mechoulam, R.; and Irene, Y., *Halogenation of phenols and Phenyl ethers with Potassium Halides in the Presence of 18-Crown-6 on Oxidation with m-Chloroperbenzoic Acid, J. Chem. Soc., Perkin Trans. 1* 1987, 1423-1427.

Muller-Vahl KB, Kolbe H, Schneider U, Emrich, HM Cannabis in movement disorders. Porsch. Kompicmentarmed (1999) 6 (suppl. 3) 23-27. (abstract only).

Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Nahas G, *Marijuana and Medicine*; 1999, *Human Press Inc.*, Totowa, NJ.

Neunhoeffer O., Gottschlich R.; "Acylating activity of O-acylated hydroxylamine derivatives"; Justus Liebigs Ann. Chem.; 736; 100-109; 1970; in German with English abstract.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

Pacheco M, et al; "Aminoalkylindoles: Actions on Specific G-Protein-Linked Receptors"; J. Pharmacol. Exp. Ther.; vol. 257, No. 1, pp. 170-183 (1991).

Palmer et al; "Natural and Synthetic Endocannabinoids and Their Structure-Activity Relationships"; Current Pharmaceutical Design; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

Pertwee; Pharmacology of cannabinoid CB1 and CB2 receptors; Pharmacol. Ther., vol. 74(2); pp. 129-180; (1997); XP002226467.

Petrov, M.L., Terent'eva, N. A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Pinnegan-Ling D, Musty R.; *Marinol and phantom limb pain: a case study. Proc Inv. Cannabinoid Rea. Sec.* (1994):53.

Pinto et al; Cannabinoid Receptor Binding and Agonist Activity of Amides and Esters of Arachidonic Acid; Mol. Pharmacol.; 1994; 46(3); 516-522.

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labelled cannabinoids"; Journal of Labellled Compounds; vol. 11(4); 551-575; 1975; XP002123229.

Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

Razdan et al; "Drugs derived from cannabinoids. 6. .Synthesis of cyclic analogues of dimethylheptylpyran"; J. Med. Chem.; vol. 19(5); 719-721; 1976 (abstract only).

Razdan et al; "Pharmacological and Behavioral Evaluation of Alkylated Anandamide Analogs"; Life Sci.; 1995; 56(23-24); 2041-2048.

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Rice AS. Cannabinoids and pain. Curr Opin Investig Drugs. 2001 Mar;2(3):399-414. (abstract only).

Richardson JD, Aanonsen I, Hargreaves KM; "Antihyperalgesic effects of a spinal cannabinoids"; Eur. J. Pharmacol. (1998) 346:145-153.

Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

Schuel, H., Burkman, L.J., Picone, R.P., Bo, T, Makriyannis, A., *Cannabinoid receptors in human sperm. Mol. Biol. Cell.*, (1997) (8), 325a.

Serdarevich B., Caroll K.K., "Synthesis and characterization of 1- and 2- monoglycerides of anteiso fatty acids"; J. Lipid Res.; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

Shen M. Thayer SA: Cannabinoid receptor agonists protect cultured rat hippocampal neurons from excitotoxicity. Mol. Pharmacol (1996) 54:459-462.

Sheskin, T. et al; Structural Requirements for Binding of Anandamide Type Compounds to the Brain Cannabinoid Receptor; J. Med. Chem.; 1997; 40; 659-667.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

Smith P.B. et al; "The pharmacological activity of anandamide, a putative endogenous cannabinoid, in mice"; Journal of Pharmacology and Experimental Therapeutics; vol. 270(1):219-227; 1994.

Terranova J-P, Storme J-J Lafon N et al; "Improvement of memory in rodents by the selective CB1 cannabinoid receptor antagonist, SR 141716"; Psycho-pharmacol (1996) 126:165-172 (abstract only).

Tetko, I. V. et al; "Volume Learning Algoritm Artificial Neural Networks for 3D QSAR Studies"; J. Med. Chem.; vol. 44, No. 15 (2001) pp. 2411-2420.

Tius et al; "Conformationally restricted hybrids of CP-55,940 and HHC: Steroeselective synthesis and activity"; Tetrahedron; 50 (9); 2671-2680; (1994) (abstract only).

Twitchell, W. et al; "Cannabinoids inhibit N- and P/Q type calcium channels in cultured rat hippocampal neurons"; Journal of Neurophysiology; 78(1); 43-50; 1997 (abstract only).

Ueda, N., Endocannabinoid hydrolases. Prostaglandins & Other Lipid Mediators 2002;68-69:521-534 (abstract only).

Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

Wagner JA, Varga K, Jarai Z, Kunos G; "Mesenteric Vasodilation Mediated by Endothelia Anandamide Receptors"; Hypertension (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(-)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

* cited by examiner

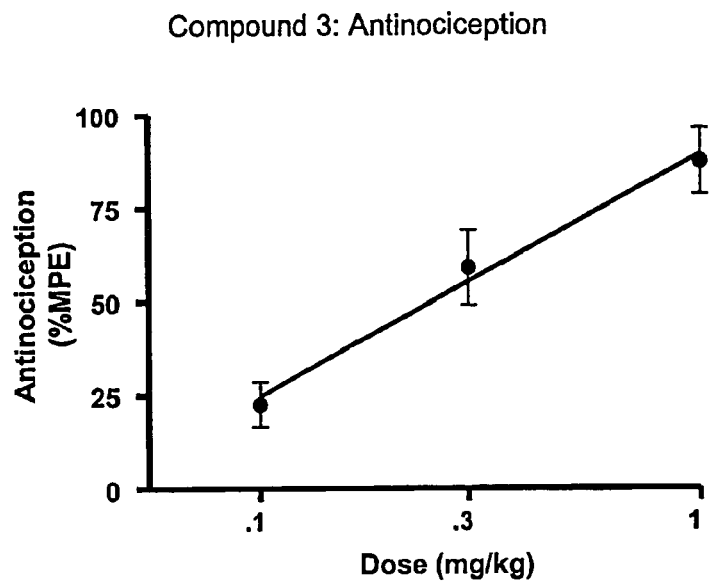

Figure 1: Peripheral antinociceptive effect of compound 3. Compound 3 was injected into the hindpaw ipsilateral to the side of nociceptive testing. Data expressed as mean ±SEM. $N$ = 6 per group.

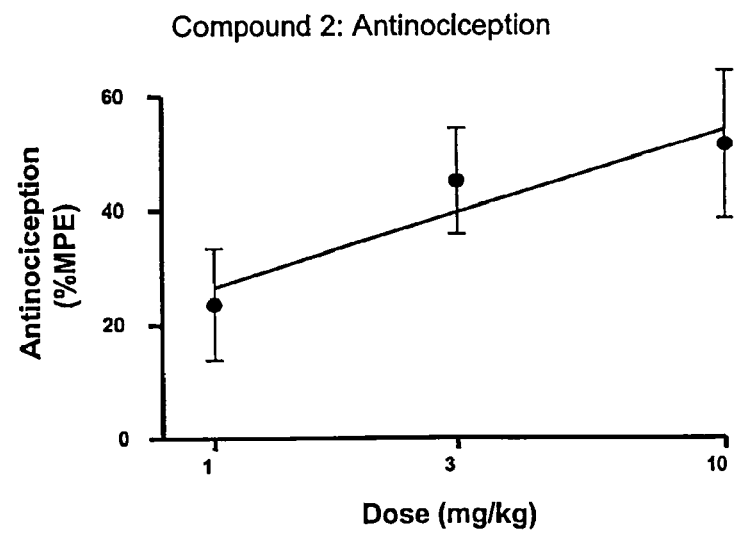

Figure 2: Peripheral antinociceptive effect of compound 2. Compound 2 was injected into the hindpaw ipsilateral to the side of nociceptive testing. Data expressed as mean ±SEM. $N$ = 6 per group.

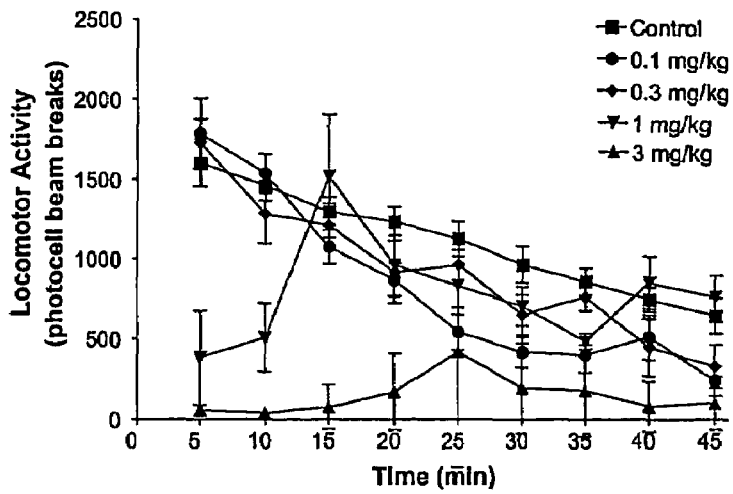

Figure 3: Compound 3 effects on time-course of locomotor activity. The line graph shows locomotor activity in five groups of mice that were treated with control only, and different doses of drugs (0.1 mg/kg, 0.3 mg/kg, 1 mg/kg and 3 mg/kg). Y-axis values are mean ±SD beam crossings per minute in 5-min periods for at least nine pairs of animals per group.

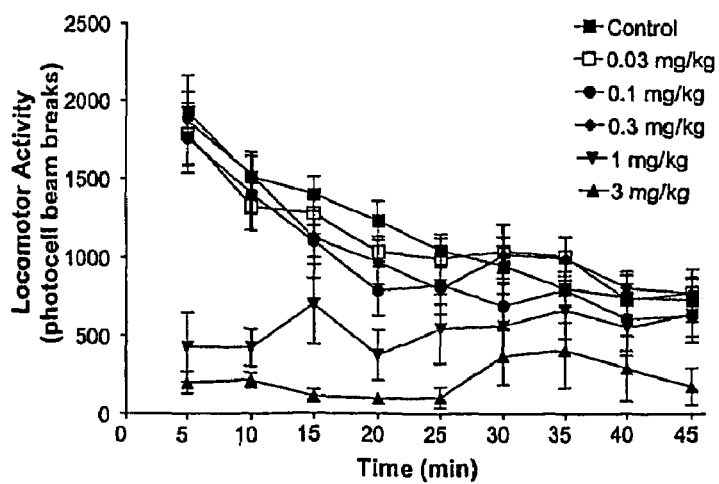

Figure 4: WIN 55212-2 effects on time-course of locomotor activity.

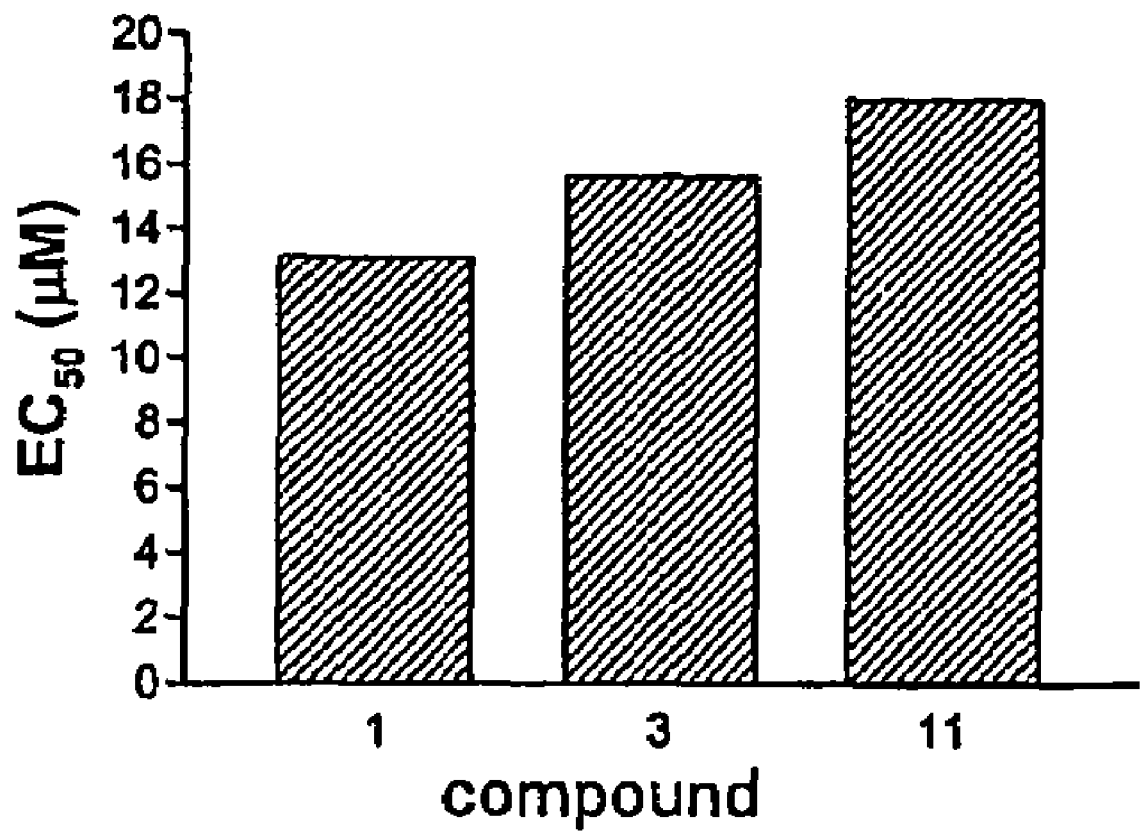

HETEROINDANES: A NEW CLASS OF POTENT CANNABIMIMETIC LIGANDS

CROSS REFERENCE TO RELATED APPLICATIONS

This application is the U.S. National Stage of International Application No. PCT/US02/34395, filed Oct. 28, 2002, which claims the benefit of U.S. Provisional Application No. 60/348,869, filed Oct. 26, 2001, the contents of each of which are incorporated herein by reference in their entirety.

FIELD OF THE INVENTION

The present invention relates generally to compounds exhibiting cannabimimetic activity and is more particularly concerned with new and improved heteroindane analogs exhibiting high binding affinities for cannabinoid receptors, pharmaceutical preparations employing these compounds and methods of administering therapeutically effective amounts of these compounds to provide a physiological effect.

BACKGROUND OF THE INVENTION

The classical cannabinoid $\Delta^9$-Tetrahydrocannabinol ($\Delta^9$-THC) is the major active constituent extracted from Cannabis sativa. The effects of cannabinoids such as $\Delta^9$-THC are due to an interaction with specific high-affinity receptors. Presently, two cannabinoid receptors have been characterized: CB1, a central receptor found in the mammalian brain and a number of other sites in the peripheral tissues and CB2, a peripheral receptor found principally in cells related to the immune system. The CB1 receptor is believed to mediate the psychoactive properties, associated with classical cannabinoids. Characterization of these receptors has been made possible by the development of specific synthetic ligands such as the agonists WIN 55212-2 and CP 55,940.

In addition to acting at the cannabinoid receptors, some cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of some cannabinoids also limit their therapeutic value.

The pharmacological effects of cannabinoids pertain to a variety of areas such as the central nervous system, the cardiovascular system, the immune system and/or the endocrine system.

SUMMARY OF THE INVENTION

Briefly stated, one aspect of the present invention comprises novel cannabimimetic ligands. The inventive compounds are encompassed by an indole structure with one or more heteroatoms in one or both of the structure rings wherein at least one additional nitrogen atom is in the ring 2, 3, 4, 5, 6 or 7 position. Some advantageous embodiments of the invention are shown in compound formulas I, II or III. R2 may be in the 2 or 3 position where possible. Representative ring positions are shown in compound formula I.

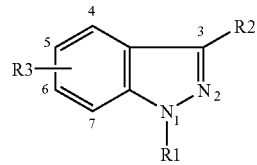

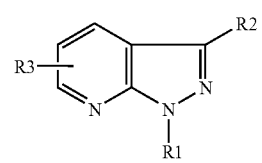

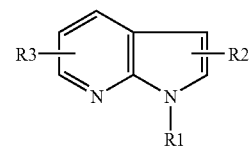

R1 comprises -Q-Z.

Q comprises an optionally present alkyl group having 1 to about 7 carbon atoms if present.

Z comprises, in any possible position, any possible member selected from H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1X_2$, NH-acyl, NH-aroyl, alkoxy, alkylmercapto, alkylamino or di-alkylamino.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of the invention R1 comprises -Q-Z.

Q comprises an optionally present alkyl group having 1 to about 7 carbon atoms if present.

Z comprises, in any possible position, any possible member selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; or any above group substituted on at least one available ring carbon atom by an alkyl group and independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; and wherein the connecting point to the Z group can be any possible ring atom.

In a variation of the invention R1 comprises -Q-Z.

Q comprises an optionally present alkyl group having1 to about 7 carbon atoms if present.

Z comprises, in any possible position, any possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group comprising a substituent group, on at least one available ring atom; and wherein the connecting point to the Z group can be any possible ring atom.

In one advantageous embodiment of the above variation Z comprises adamantyl or heteroadamantyl.

In a variation of the invention R1 comprises -Q-Z.

Q comprises an optionally present alkyl group having 1 to about 7 carbon atoms if present.

Z comprises, in any possible position, any possible member selected from

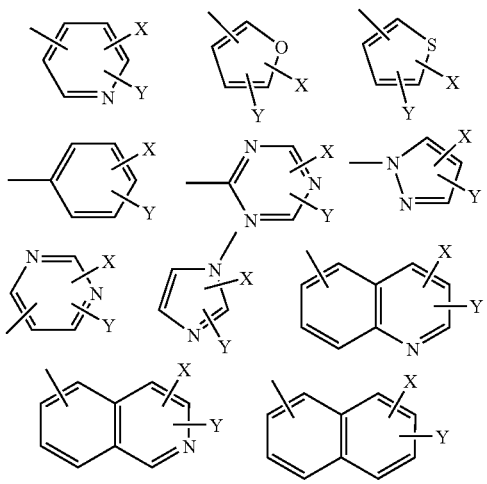

wherein X and Y in the Z structure each independently comprise H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, OalkylN$X_1X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

R2 comprises -$Q_1$-het-$Q_2$-Z.

$Q_1$ comprises an optionally present alkyl group having 1 to about 5 carbon atoms if present.

het comprises O, N or S.

$Q_2$ comprises an optionally present alkyl group having 1 to about 5 carbon atoms if present.

Z comprises, in any possible position, any possible member selected from H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, OalkylN$X_1X_2$, NH-acyl, NH-aroyl, alkoxy, alkylmercapto, alkylamino or di-alkylamino.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of the invention R2 comprises -$Q_1$-het-$Q_2$-Z.

$Q_1$ comprises an optionally present alkyl group having 1 to about 5 carbon atoms if present.

het comprises O, N or S.

$Q_2$ comprises an optionally present alkyl group having 1 to about 5 carbon atoms if present.

Z comprises, in any possible position, any possible member selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; or any above group substituted on at least one available ring carbon atom by an alkyl group and independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; and wherein the connecting point to the Z group can be any possible ring atom.

In a variation of the invention R2 comprises -$Q_1$-het-$Q_2$-Z.

$Q_1$ comprises an optionally present alkyl group having 1 to about 5 carbon atoms if present.

het comprises O, N or S.

$Q_2$ comprises an optionally present alkyl group having 1 to about 5 carbon atoms if present.

Z comprises, in any possible position, any possible member selected from

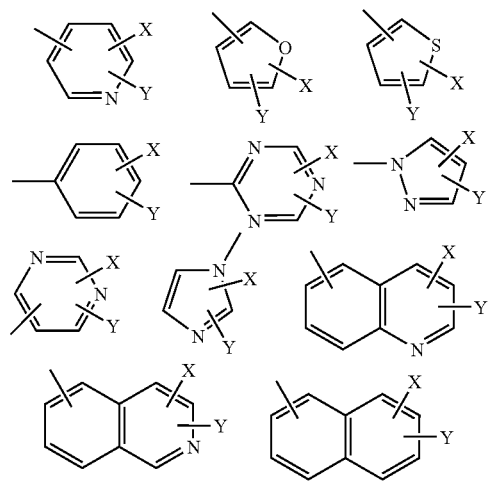

wherein X and Y in the Z structure each independently comprise H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of the invention R2 comprises $-Q_1$-het-$Q_2$-Z.

$Q_1$ comprises an optionally present alkyl group having 1 to about 5 carbon atoms if present.

het comprises O, N or S.

$Q_2$ comprises an optionally present alkyl group having 1 to about 5 carbon atoms if present.

Z comprises, in any possible position, any possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom; and wherein the connecting point to the Z group can be any possible ring atom.

In one advantageous embodiment of the above variation Z comprises adamantyl or heteroadamantyl.

In a variation of the invention R2 comprises $-Q_1$-X-$Q_2$-Z.

$Q_1$ comprises an optionally present alkyl group having 1 to about 5 carbon atoms if present.

$Q_2$ comprises an optionally present alkyl group having 1 to about 5 carbon atoms if present and connected to a C, O or N atom in the X group.

X is optionally present and comprises any possible member selected from C(O), C(O)O, OC(O)O, NC(O)O, C(O)NT, NTC(O), OC(O)NT, C(O)NTT, C(O)NTNT, NTC(O)NT if present.

T comprises H, an alkyl group comprising 1 to about 4 C atoms, a heteroalkyl group comprising 1 to about 4 C atoms, a carbocyclic ring having about 4 to about 7 ring members, a heterocyclic ring having about 4 to about 7 ring members, an aromatic ring having about 5 to about 7 ring members or a heteroaromatic ring having about 5 to about 7 ring members or any above group having a substituent group on at least one available ring atom.

Z comprises in any possible position, any possible member selected from H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1X_2$, NH-acyl, NH-aroyl, alkoxy, alkylmercapto, alkylamino or di-alkylamino.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

In a variation of the invention R2 comprises $-Q_1$-X-$Q_2$-Z.

$Q_1$ comprises an optionally present alkyl group having 1 to about 5 carbon atoms if present.

$Q_2$ comprises an optionally present alkyl group having 1 to about 5 carbon atoms if present and connected to a C, O or N atom in the X group.

X is optionally present and comprises any possible member selected from C(O), C(O)O, OC(O)O, NC(O)O, C(O)NT, NTC(O), OC(O)NT, C(O)NTT, C(O)NTNT, NTC(O)NT if present.

T comprises H, an alkyl group comprising 1 to about 4 C atoms, a heteroalkyl group comprising 1 to about 4 C atoms, a carbocyclic ring having about 4 to about 7 ring members, a heterocyclic ring having about 4 to about 7 ring members, an aromatic ring having about 5 to about 7 ring members or a heteroaromatic ring having about 5 to about 7 ring members; or any above group having a substituent group on at least one available ring atom.

Z comprises, in any possible position, any possible member selected from 1-, 2- or 3-pyrrolidinyl, 1-, 2-, 3- or 4-piperidinyl, 2-, 3- or 4-morpholinyl, 2-, 3-, or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; or any above group substituted on at least one available ring carbon atom by an alkyl group and independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; and wherein the connecting point to the Z group can be any possible ring atom.

In a variation of the invention R2 comprises $-Q_1$-X-$Q_2$-Z.

$Q_1$ comprises an optionally present alkyl group having 1 to about 5 carbon atoms if present.

$Q_2$ comprises an optionally present alkyl group having 1 to about 5 carbon atoms if present and connected to a C, O or N atom in the X group.

X is optionally present and comprises any possible member selected from C(O), C(O)O, OC(O)O, NC(O)O, C(O)NT, NTC(O), OC(O)NT, C(O)NTT, C(O)NTNT, NTC(O)NT if present.

T comprises H, an alkyl group comprising 1 to about 4 C atoms, a heteroalkyl group comprising 1 to about 4 C atoms, a carbocydic ring having about 4 to about 7 ring members, a heterocyclic ring having about 4 to about 7 ring members, an aromatic ring having about 5 to about 7 ring members or a heteroaromatic ring having about 5 to about 7 ring members, or any above group having a substituent group on at least one available ring atom.

Z comprises, in any possible position, any possible member selected from

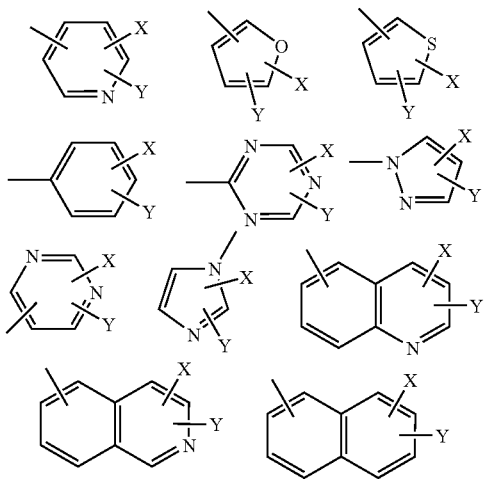

wherein X and Y in the Z structure each independently comprise H, halogen, $N_3$, NCS, CN, $NO_2$, $NX_1X_2$, $OX_3$, OAc, NHCOalkyl, CHO, $CF_3$, $COOX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, OalkylNX$_1$X$_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl hydroxyloweralkyl, or alkyl-$NX_1X_2$.

In a variation of the invention R2 comprises -$Q_1$-X-$Q_2$-Z.

$Q_1$ comprises an optionally present alkyl group having 1 to about 5 carbon atoms if present.

$Q_2$ comprises an optionally present alkyl group having 1 to about 5 carbon atoms if present and connected to a C, O or N atom in the X group.

X is optionally present and comprises any possible member selected from C(O), C(O)O, OC(O)O, NC(O)O, C(O)NT, NTC(O), OC(O)NT, C(O)NTT, C(O)NTNT, NTC(O)NT if present.

T comprises H, an alkyl group comprising 1 to about 4 C atoms, a heteroalkyl group having 1 to about 4 C atoms, a carbocyclic ring having about 4 to about 7 ring members, a heterocyclic ring having about 4 to about 7 ring members, an aromatic ring having about 5 to about 7 ring members or a heteroaromatic ring having about 5 to about 7 ring members; or any above group having a substituent group on at least one available ring atom.

Z comprises, in any possible position, any possible member selected from a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group comprising a substituent group on at least one available ring atom; and wherein the connecting point to the Z group can be any possible ring atom.

In one advantageous embodiment of the above variation Z comprises adamantyl or heteroadamantyl.

In one advantageous embodiment of the above variation Z comprises phenyl having independently selected substituent groups in at least one of the 2 and 5 positions.

In one advantageous embodiment of the above variation Z comprises phenyl substituted with a heteroaromatic moiety.

In one advantageous embodiment of the above variation Z comprises phenyl substituted in one of the 2 or 5 position with a heteroaromatic moiety and in the other of the 2 or 5 position with a halogen.

R3 comprises a substituent at any or all of the possible 4-, 5-, 6- and/or 7-positions. Each substituent is independently selected from H, halogen, $N_3$, NCS, CN, $NO_2$, $NX_1X_2$, $OX_3$, OAc, NHCOalkyl, CHO, $CF_3$, $COOX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, OalkylNX$_1$X$_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms.

$X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

The inventive compounds include any and all isomers and steroisomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in prior art compositions or that are otherwise not necessary to the achievement of the function and/or objectives of the present invention.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 16 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated. The alkyl group can be unsubstituted, singly substituted or, if possible, multiply substituted, with substituent groups in any possible position. Unless otherwise specifically limited, a cyclic alkyl group includes monocyclic, bicyclic, tricyclic, tetracyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or napthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include naphthalene and bicyclooctane.

Unless otherwise specifically defined, a carbocyclic ring is a non-aromatic ring structure, saturated or unsaturated, having about 3 to about 8 ring members that includes only carbon as ring atoms, for example, benzene or cyclohexane. The carbocyclic ring can be unsubstituted, singly substituted or, if possible, multiply substituted, with substituent groups in any possible position.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members independently selected from carbon atoms and one or more heteroatoms, including oxygen, nitrogen and/or sulfur, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused rings having ring members independently selected from carbon and one or more heteroatoms, including oxygen, nitrogen and/or sulfur. The heterobicyclic ring structure may be saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include isobenzofuran, indole, tetrahydroisoquinoline, tropane and homotropane.

Unless otherwise specifically defined, a heterocyclic ring is a saturated ring structure having about 3 to about 8 ring members independently selected from carbon atoms and one or more heteroatoms, including oxygen, nitrogen and/or sulfur; for example, piperidine, morpholine, piperazine, pyrrolidine, thiomorpholine, and their derivatives. The heterocyclic ring can be unsubstituted, singly substituted or, if possible, multiply substituted, with substituent groups in any possible position.

Unless otherwise specifically defined, a heterotricyclic ring structure comprises 3 fused rings having ring members independently selected from carbon and one or more heteroatoms, including oxygen, nitrogen and/or sulfur. The heterotricyclic ring structure may be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline and phenazine.

Unless otherwise specifically defined, a heteropolycyclic ring structure comprises more than 3 fused rings having ring members Independently selected from carbon and one or more heteroatoms, including oxygen, nitrogen and/or sulfur. The heteropolycyclic ring structure is typically unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantane, other heteroadamantanes, tropane and homotroapane.

Unless otherwise specifically defined, the term "optionally present" means that the specified moiety may or not be present in the recited structure. For example, if the recited structure is alkyl-V—W with V being optionally present, the recited structure comprises alkyl-V—W as well as alkyl-W.

Unless otherwise specifically defined, the term "phenacyl" refers to the general formula -phenyl-acyl.

Unless otherwise specifically defined, a polycyclic ring structure comprises more than 3 fused rings and includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantane, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 fused rings and includes carbon as ring atoms. The tricyclic ring structure can be saturated or unsaturated. The tricyclic ring structure can be unsubstituted, singly substituted or, if possible, multiply substituted, with substituent groups in any possible position, and may be substituted or unsubstituted. The individual rings may or may not be of the same type. Examples of tricyclic ring structures include fluorene and anthracene.

Substituent groups for the above moieties useful in the invention are those groups that do not significantly diminish the biological activity of the inventive compound. Substituent groups that do not significantly diminish the biological activity of the inventive compound include, for example, H, halogen, $N_3$, NCS, CN, $NO_2$, $NX_1X_2$, $OX_3$, OAc, O-acyl, O-aroyl, OalkylOH, OalkylN$X_1X_2$, NH-acyl, NH-aroyl, NHCOalkyl, CHO, $CF_3$, $COOX_3$, $SO_3X_3$, $PO_3X_1X_2$, $OPO_3X_1X_2$, $SO_2NX_1X_2$ $NCONX_1X_2$, $CONX_1X_2$, alkyl, alcohol, alkoxy, alkylmercapto, alkylamino, di-alkylamino, sulfonamide, thioalkoxy, acyl, substituted acyl, aroyl, substituted aroyl, heteroaroyl, substituted heteroaroyl, aryl, substituted aryl, heteroaryl (including tetrazoles and alkyltetrazoles), substituted heteroaryl, phenyl, heterocyclic rings or methylene dioxy when the substituted structure has two adjacent carbon atoms, wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and X2 together comprise part of an imide ring having about 5 to about 6 members and $X_3$ comprises H, alkyl, hydroxylower-alkyl, or alkyl-$NX_1X_2$. Unless otherwise specifically limited a substituent group may be in any possible position.

Some of the inventive compounds show high binding affinities for the CB1 and CB2 cannabinoid receptors. More specifically, some of the inventive analogs show similar or higher receptor binding affinity than the well-known indole cannabinoid WIN 55212-2. Thus, another aspect of the invention Is use of at least one of the inventive compounds to interact with cannabinoid receptors.

Further, some of the inventive heteroindane analogs show a surprisingly higher selectivity for one of the cannabinoid receptors. These inventive selective analogs are able to interact with one cannabinoid receptor, for example the CB2 cannabinoid receptor, without affecting the other cannabinoid receptor to the same degree. Therefore, still another aspect of the invention is use of at least one of the inventive compounds to preferentially interact with one cannabinoid receptor.

Some of the novel heteroindanes described herein are cannabinoid receptor agonists. The inventive heteroindane agonists interact with the CB1 and/or CB2 cannabinoid receptor binding site to initiate a physiological or a pharmacological response characteristic of that receptor. Therefore, a further aspect of the invention is use of at least one of the inventive compounds to initiate an agonistic response from a cannabinoid receptor.

Some of the novel heteroindanes described herein are cannabinoid receptor antagonists. The inventive heteroindane antagonists interact with the CB1 and/or CB2 cannabinoid receptor binding site to block other ligands from the receptor binding site without initiating a physiological or a pharmacological response characteristic of that receptor. Thus, cannabinoid antagonists typically oppose the cannabinoid receptor site response characteristics initiated by cannabinoid agonists or cannabinoid inverse agonists. Therefore, a further aspect of the invention is use of at least one of the inventive compounds to oppose initiation of an agonistic or inverse agonistic response from a cannabinoid receptor.

The inventive heteroindane analogs described herein, and physiologically acceptable salts thereof, have pharmacological properties when administered in therapeutically effective amounts for providing a physiological response in individuals and/or animals. Thus, another aspect of the invention is the administration of a therapeutically effective amount of at least one of the inventive compounds, or a physiologically acceptable salt thereof, to an individual or animal to provide a physiological response.

A better understanding of the invention will be obtained from the following detailed description of the article and the desired features, properties, characteristics, and the relation of the elements as well as the process steps, one with respect to each of the others, as set forth and exemplified in the description and illustrative embodiments.

BRIEF DESCRIPTION OF THE DRAWINGS

FIG. 1 shows the peripheral antinociceptive effect of disclosed compound 3;

FIG. 2 shows the peripheral antinociceptive effect of disclosed compound 2;

FIG. 3 shows the effects of disclosed compound 3 on time-course of locomotor activity;

FIG. 4 shows the effects of WIN 55212-2 on time-course of locomotor activity; and FIG. 5 shows the $EC_{50}$ values of disclosed compounds 1, 3 and 11 for stimulating [$^{35}$S] GTPγS binding in rat microsomal membranes.

DESCRIPTION OF SOME PREFERRED EMBODIMENTS

As used herein a "therapeutically effective amount" of a compound, is the quantity of a compound which, when administered to an individual or animal, results in a sufficiently high level of that compound in the individual or animal to cause a physiological response. Some physiological responses that result from cannabinoid receptor (CB1 and/or CB2) interaction with agonist or antagonist compounds include: relief of central pain; peripheral pain; inflammatory pain; neuropathy; alleviation of the symptoms of neurodegenerative diseases including multiple sclerosis, Parkinson's disease, Huntington's chorea, Alzheimer's disease; alleviation of the symptoms of mental disorders such as schizophrenia and depression; reduction or prevention of endotoxic shock and hypotensive shock; appetite modulation; fertility reduction; reduction or prevention of diseases associated with motor function such as Tourette's syndrome; reduction or prevention of inflammation; neuroprotection; suppression of memory; production of peripheral vasodilation; reduction of intraocular pressure in glaucoma; relief of nausea associated with cancer chemotherapy, enhancement of appetite in AIDS wasting syndrome; and reduction of spasticity in multiple sclerosis and epilepsy.

Typically, a "therapeutically effective amount" of an inventive compound is believed to range from about 5 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including, for example, orally, rectally, transdermally or by parenteral routes. (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

The following examples are given for purposes of illustration only in order that the present invention may be more fully understood. These examples are not intended to limit in any way the scope of the invention unless otherwise specifically indicated.

EXAMPLES

TABLE 1 illustrates some synthesized heteroindane analogs of the present invention (compounds 1-11).

TABLE 1

| | | Ki (nM) | |
|---|---|---|---|
| | | CB1 | CB2 |
| 1 | indazole-3-carboxamide-N-adamantyl, N1-(2-morpholinoethyl) | 6.84 | 0.147 |
| 2 | indazole-3-carboxamide-N-adamantyl, N1-((1-methylpiperidin-2-yl)methyl) | 47.5 | 8.74 |
| 3 | indazole-3-carboxamide-N-adamantyl, N1-(3-cyanopropyl) | 2.28 | 0.309 |
| 4 | indazole-3-carboxamide-N-adamantyl, N1-(3-chloropropyl) | 1.65 | 1.34 |
| 5 | indazole-3-carboxamide-N-adamantyl, N1-(3-iodopropyl) | 0.596 | 0.164 |
| 6 | indazole-3-carboxamide-N-adamantyl, N1-(3-(dimethylamino)propyl) | 443 | 20.9 |

TABLE 1-continued

| | | Ki (nM) | |
|---|---|---|---|
| | | CB1 | CB2 |
| 7 | indazole-3-carboxamide-N-(1-naphthyl), N1-(3-chloropropyl) | 0.268 | 0.135 |
| 8 | indazole-3-carboxamide-N-(1-naphthyl), N1-(3-iodopropyl) | 13.7 | 27.0 |
| 9 | indazole-3-carboxamide-N-(1-naphthyl), N1-(3-(dimethylamino)propyl) | 450.6 | 234.6 |
| 10 | indazole-3-carboxamide-N-(1-naphthyl), N1-((1-methylpiperidin-2-yl)methyl) | 15.0 | 8.04 |
| 11 | 6-bromo-1-phenyl-indazole-3-carboxamide-N-piperidinyl | 1846 | 84.7 |

Another synthesized heteroindane analog (12) is 1-(N-Methyl-2-piperidinylmethyl)-3(2-iodobenzoyl) indazole.

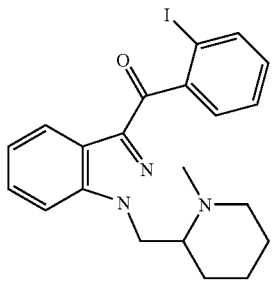

KI (nM): CB1 9.120; CB2 22.15

The inventive analogs were tested for CB2 receptor binding affinity and for CB1 receptor affinity (to determine selectivity for the CB2 receptor). As used herein, "binding affinity" is represented by the $IC_{50}$ value which is the concentration of an analog required to occupy the 50% of the total number (Bmax) of the receptors. The lower the $IC_{50}$ value the higher the binding affinity. As used herein an analog is said to have "binding selectivity" if it has higher binding affinity for one receptor compared to the other receptor; e.g. a cannabinoid analog which has an $IC_{50}$ of 0.1 nM for CB1 and 10 nM for CB2, is 100 times more selective for the CB1 receptor. For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinold receptor was assessed as described in W. A. Devane et al, *Determination and Characterization of a Cannabinoid Receptor in a Rat Brain*, Mol. Pharmacol., 34, 605-613 (1988) and A. Charalambous et al, *5'-azido $\Delta^{8-}$ THC: A Novel Photoaffinity Label for the Cannabinoid Receptor*, J. Med. Chem., 35, 3076-3079 (1992) with the following changes. The above articles are incorporated by reference herein.

Membranes, previously frozen at –80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 µg of membranes were incubated in silanized 96-well microtiter plate with TME containing 0.1% essentially fatty acid-free bovine serum albumin (BSA), 0.8 nM [$^3$H] CP-55,940, and various concentrations of test materials in a final volume of 200 mL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two indeperident experiments performed in duplicate was used to calculate $IC_{50}$ values which were converted to $K_i$ values using the assumptions of Cheng et al, *Relationship Between the Inhibition Constant ($K_i$) and the concentratiori of Inhibitor which causes 50% Inhibition ($IC_{50}$) of an Enzymatic Reaction*, Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM). The cannabinoid receptor binding affinities (Ki) for synthesized analogs 1-11 are listed in TABLE 1.

Some inventive heteroindane analogs were also subjected to a GTPγS binding assay as described below. The GTPγS binding assay generally followed the procedures of S. Lin et al, *Novel Analogues of Arachidonylethanolamide (Anandamide): Affinities for the CB1 and CB2 Cannabinoid Receptors and Metabolic Stability*, J. Med. Chem., 41, 5353-5361 (1998) and M. A. K. Markwell et al, *A Modification of the Lowry Procedure to Simplify Protein Determination in Membrane and Lipoprotein Samples*, Anal. Biochem. 87, 206-210 (1978), the contents of which are hereby incorporated by reference. The results indicated that all compounds tested were agonists for both the CB1 and the CB2 receptors.

The inventors believe that the novel heteroindane analogs when studied for their effects on the level of cyclic AMP in order to assess their functional potency as agonists or antagonists will confirm that the prepared compounds act as agonists.

Procedure for [$^{35}$S] GTPγS Binding Assay:
1. Cerebellar Membrane Preparation. The striped rat brains were slightly thawed, and using a spatula, the cerebellum was removed and discarded; the remaining tissue was homogenized in ice-cold homogenization buffer (0.32 M sucrose, 10 mM Tris, 5 mM EDTA, pH 7.4). The homogenate suspension was centrifuged at 3700 g for 10 min. The supernatant was decanted, and 12 mL was layered over 10 mL of 1.2 M sucrose. These tubes were centrifuged in an L7-65 ultracentrifuge using a 50.2 Ti rotor at 4° C. for 29 min at 44 000 rpm. The layer at the interface was then removed and subjected to a second sucrose spin over 0.8 M sucrose. The pellet was resuspended in TME buffer (25 mM Tris base, 5 mM $MgCl_2$, 1 mM EDTA, pH 7.4), aliquoted, and stored at –70° C. Protein was determined using the method of Markwell et al.
2. [$^{35}$S]GTPγS Binding Assay. The rat membrane preparation (40-50 µg of protein) was incubated for1 h at 30° C. in assay buffer (10 mM Tris, 100 mM NaCl, 5 mM $MgCl_2$, 0.1% BSA) with 50 µL of 50 µM GDP, 50 µL of 0.05 nM [$^{35}$S]GTPγS, or 100 µL of either; 10 µM GTPγS was used to measure the nonspecific binding, a series of different concentrations of the analogues being tested, or buffer alone as a control to obtain the baseline of GTPγS simulation. The reaction was terminated by rapid filtration through Whatman GF/B filters, with ice-cold wash buffer containing 0.5% bovine serum albumin using the Packard Filtermate. Bound radioactivity was measured on the Packard Top-Count microplate scintillation counter.

TABLE 2 illustrates $EC_{50}$ values of inventive compounds 1, 3 and 11 for stimulating [$^{35}$S] GTPγS binding in rat microsomal membranes. The results are shown graphically in FIG. 5.

TABLE 2

| compound | EC50 (µM) | | |
| --- | --- | --- | --- |
| | Y | SD | N |
| 1 | 13.088 | 8.959 | 3 |
| 3 | 15.600 | 7.142 | 3 |
| 11 | 17.973 | 4.655 | 3 |

Prepatation of Compounds

Genetal. Column chromatography was carried out by using active silica gel (230-400 mesh) available from Selecto Scientific of Suwanee, Ga. Eluents were distilled before use. Solvents for reactions were dried or purified as required. Reactions were carried out under argon atmosphere unless otherwise noted. All of the reagents are available from Sigma-Aldrich Fine Chemicals of Milwaukee, Wis. and/or Lancaster Synthesis Inc. of Windham, N.H.

General procedure for the preparation of compounds 1-10:

Int B.

To a magnetically stirred solution of 1 H-Indazole-3-carboxylic acid (3.00 g, 18.5 mmol), 1-aminonaphthalene (2.65 g, 18.5 mmol) and 1-hydroxybenzotriazole (HOBt; 3 g, 22.2 mmol) in dry DMF (45 mL) was added 1-ethoxy-3-[3-(dimethylamino)propyl]carbodiimide hydrochloride (WSCD.HCl; 3.9 g, 20.3 mmol) at 0° C. After addition, the reaction mixture was stirred at room temperature for 2 h. After stirring for 2 h brine was added and the mixture was extracted multiple times with dichloromethane. The combined extracts were washed with brine, dried over anhydrous sodium sulfate, filtered, and evaporated. Purification by flash column chromatography on silica gel gave the expected Int B.

Final Compound 1-10:

To a magnetically stirred solution of 0.51 mmol of Int A or B in 2 mL of DMF at room temperature was added NaH (60% dispersion in mineral oil, 25 mg, 0.63 mmol). The resulting mixture was allowed to stir at room temperature for 3 h. The reaction mixture was cooled to about 20° C., and RX (0.56 mmol) was added. The resulting solution was allowed to stir at room temperature for about 18 h. The DMF was evaporated under reduced pressure, and the residue was dissolved in $CH_2Cl_2$. The solution was washed sequentially with 10% aqueous sodium carbonate solution, water and brine, dried Scheme 1:

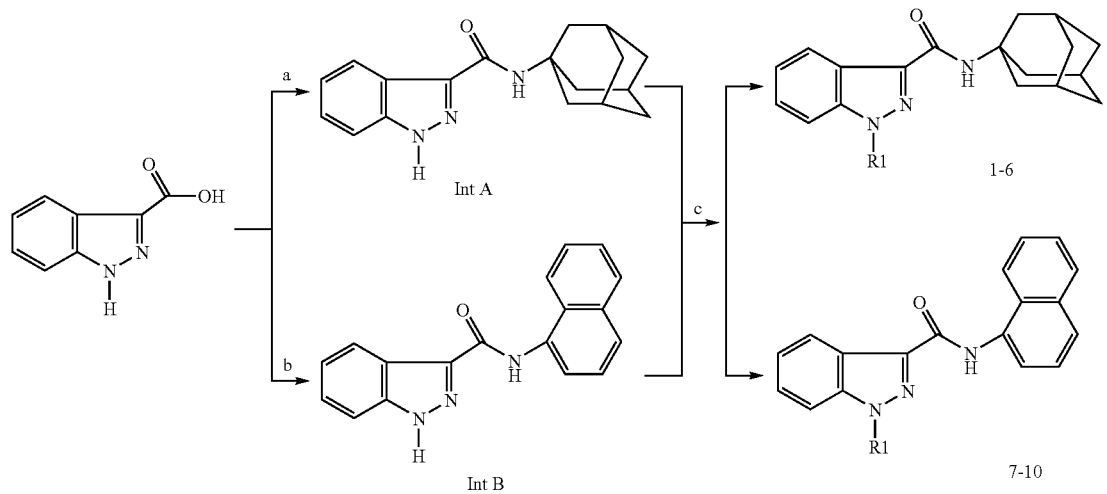

a CO(imd)₂/DMF, adamantamine; b 1-HOBt, WSCD•HCl, DMF, 1-aminonaphthalene; c NaH/DMF, RX (alkyl halide)

InA.

To a magnetically stirred solution of 1H-Indazole-3-carboxylic acid (1 g, 6.17 mmol) in EMF (15 mL) was added 1,1'-carbonyldiimidazole (1.1 g, 6.78 mmol) in one portion. The resulting solution was warmed at 60° C. for 2 hours (h) and then cooled to room temperature before adding a suspension of adamantamine (0.932 g, 6.17 mmol) in DMF (20 mL). The resulting solution was heated at 60° C. for 2 h. The DMF was evaporated under reduced pressure and the residue dissolved in $CH_2Cl_2$. The solution was washed sequentially with water, 1 N NaOH solution, water, and brine, dried ($Na_2SO_4$), filtered, and evaporated under reduced pressure. The residue was recrystallized from EtOH to give the expected Int A.

($Na_2SO_4$), filtered, and evaporated under reduced pressure to give an oil. The resulting product was purified by flash column chromatography.

General procedure for the preparation of compound 11:

Scheme 2:

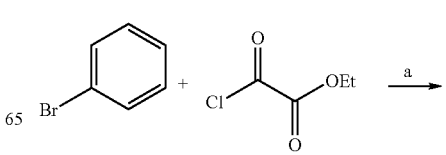

-continued

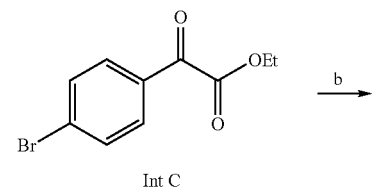
Int C

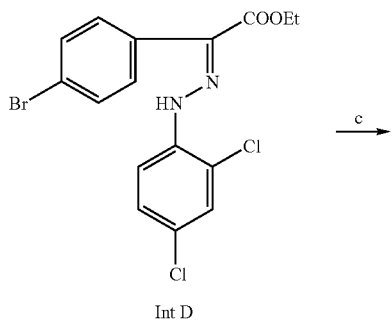
Int D

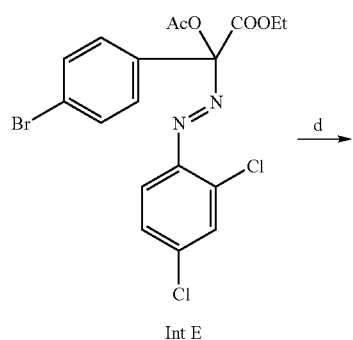
Int E

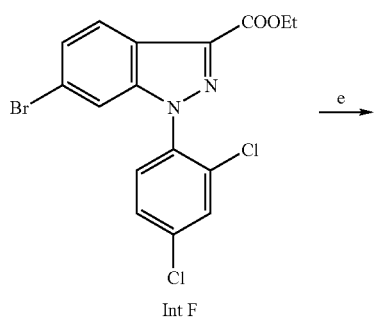
Int F

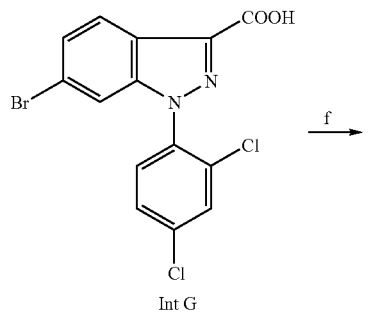
Int G

-continued

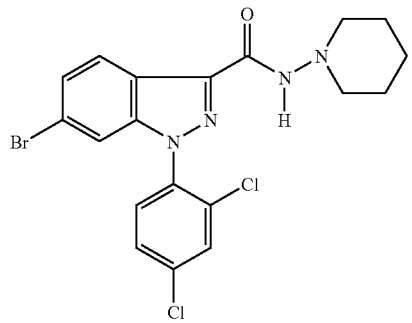
11 a AlCl$_3$/CH$_2$Cl$_2$; b HAc/MeOH, 2,4-dichlorophenylhydrazine; c Pb(OAc)$_4$/CH$_2$Cl$_2$; d BF$_3$•Et$_2$O/Et$_2$O; e KOH/H$_2$O, then HCl/H$_2$O; f CO (imd)$_2$/DMF, 1-aminopiperidine.

Int C.

Bromobenzene (2.1 g, 13 mmol), 2.6 g (19 mmol) of ethyl oxalyl chloride, and 25 mL of anhydrous methylene chloride were placed in a 50 mL flask equipped with a magnetic stirrer and suspended in an ice-salt bath. After the solution was stirred for 10 min, 3.4 g (25 mmol) of aluminum chloride was added in small portions over 10 min. When the solution turned red-brown and became homogenous, the ice-salt bath was removed and the mixture was poured over 100 g of crushed ice and 50 ml of concentrated hydrochloric acid. The decomposed mixture was washed with 30 mL of 0.1 N sodium hydroxide three times. After the organic layer was separated and the solvent was evaporated, the crude product was purified by column chromatography to give Int C.

Int D.

Ethyl phenylglyoxylate (1.1 g, 4.28 mmol) was added to a mixture of 2,4-dichlorophenylhydrazine (0.78 g, 4.39 mmol) and 90% acetic acid (1 mL) and the solution refluxed for 30 min. Ethyl phenylglyoxylate 2,4-chlorophenylhydrazone (Int D) crystallized on cooling.

Int E.

A solution of Int D (1.27 g, 3.05 mmol) in dichloromethane (10 mL) was added to a stirred mixture of lead tetraacetate (3.59 g) and dichloromethane (20 mL), keeping the temperature between 0° C. and 10° C. The mixture was heated for 15 min at 20-25° C.; water and dilute HCl were then added with the temperature kept below 25° C. The organic layer was separated and the solvent evaporated. Purification by flash column chromatography on silica gel gave the expected Int E.

Int F.

Boron trifluoride etherate (10 mL) was added dropwise to a stirred solution of Int E (1.22 g, 2.57 mmol) in ether (25 mL), keeping the temperature at 0° C. The mixture was refluxed for 20 min, poured into water, and stirred until complete evaporation of ether has occurred. Int F was separated and purified by flash column chromatography on silica gel.

Int G.

A mixture of the above ester (0.928 g 2.24 mmol), 10% KOH aqueous (3 mL), and methanol (15 mL) was refluxed for 3 h. The cooled solution was acidified with 6 N HCl. The precipitate was collected and purified by flash column chromatography on silica gel to give Int G.

Final Compound 11.

Compound 11 was prepared by following the procedure a of Scheme 1 by using 1-aminopiperidine instead of adamantamine.

Synthesis 3-aroyl Substituted Indazoles via Cycloaddition of Diazoketones with Benzyne.

The methodology of this approach is showed below:

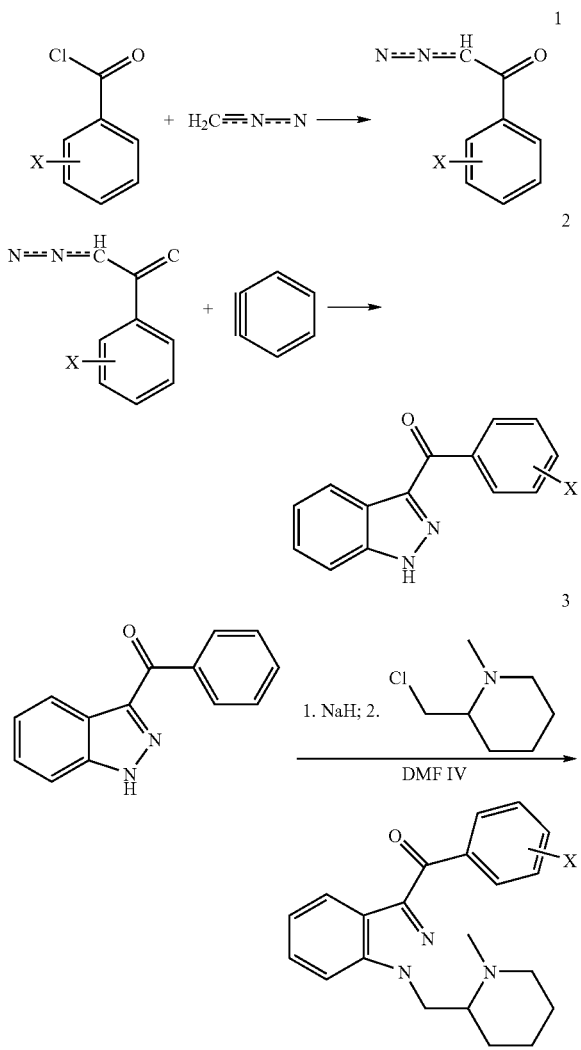

A suspension of phenyidiazonium carboxylate (5 mmol) and appropriate diazoketone (2.5 mmol) is stirred and heated at 40° C. in 20 ml methylene chloride for approximately 6 h Caution! Phenyidiazonium carboxylate is highly explosive in a dry form. Do not dry phenyldiazonium carboxylate after it is synthesized! To the reaction mixture 30 ml of water is added and products are extracted with ethyl acetate (3×10 ml). The combined organic extract is washed with water, washed with brine, dried with sodium sulphate and evaporated to dryness to give a dark oil or solid. The desired product is isolated and purified using preparative column chromatography on silica gel (petrol ether-ethyl acetate). Alkylation of the prepared product is the same as for the synthesis of indole derivatives.

Results of Antinociception Activity

Using rats as test subjects, varied doses of some of the inventive compounds were injected subcutaneously in the dorsal surface of the paw (i.paw, 50 μl). Measurements were taken 25 min after i.paw injection. Assessment of antinociceptive action was made by evaluating the response latency to removal of the paw from a focused source of thermal stimulation, as described by T. P. Malan Jr., *CB2 Cannabinoid Receptor-mediated Peridpheral Antinociception*, Pain, 93, 239-245 (2001), the content of which is incorporated by reference herein. Rats were allowed to acclimate within Plexiglas enclosures on a clear glass plate maintained at 30° C. A radiant heat source (a high-intensity projector lamp) was focused onto the plantar surface of the hindpaw. Activation of the heat source activated a timer, which stopped when withdrawal of the paw was detected with a photodetector. A maximal cut-off of 40 seconds (s) was utilized to prevent tissue damage.

Antinociception is expressed as the percent of the maximum possible effect (% MPE), using the formula: % MPE= (WL-CL)/(CO-CL), where WL is the withdrawal latency obtained experimentally, CL is the control (baseline) value before drug administration, and CO is the cut-off value (40 s). Dose-response curves were generated. Significance was defined as $P<0.05$.

As shown in FIG. 1, compound 3 produced dose-dependent antinociception to a thermal stimulus applied to the hindpaw, when administered into the hindpaw on the side of testing (ipsilateral i.paw). As shown in FIG. 2, compound 2 produced the similar dose-dependent antinociception to a thermal stimulus but was less potent than compound 3.

This antinociception and analgesic effect is attributed to the interactions of the inventive compounds with the CB1 and/or CB2 receptors. The higher affinities for cannabinoid receptors observed in compound 3 as compared to compound 2 are reflected in the more potent ability of compound 3 to produce analgesic effects (see FIGS. 1 and 2) as compared to compound 2. It should be noted that CB2 selective compounds can produce pharmacological effects by preferential interaction with the CB2 receptors without producing CNS effects. Non-selective compounds will also produce pharmacological effects, although the effects will be associated with both CB1 and CB2 receptors.

Results of Locomotor Activity

Rats were injected with varied doses of either some of the inventive compounds or with WIN 55212-2, a known CB1/CB2 receptor agonist. The injected compounds were solubilized in DMSO:40% cyclodextrin (1:10) and intravenously administered.

Locomotor activity was assessed by measuring the rate of beam crossings by rats in a photocell apparatus according to the procedure of M. Cosenza et al, *Locomotor Activity and Occupancy of Brain Cannabinoid CB1 Receptors by the Antagonist/Inverse Agonist AM281*, Synapse, 38, 477-482 (2000).

As shown in FIG. 4, WIN 55212-2, a known CB1/CB2 receptor agonist, significantly reduced locomotor activity early after administration. As shown in FIG. 3, inventive compound 3 similarly significantly reduced locomotor activity early after administration.

Both WIN 55212-2 and compound 3 acted as cannabinold agonists in the locomotor assay and produced the typical cannabinoid-like catalepsy and inhibition of locomotion. For compound 3 this locomotor effect is attributed to the interaction of that compound with the CB1 receptor in the central nervous system.

The inventive heteroindane analogs described herein also have potential as immunomodulating drugs and antiinflammatory agents. Additionally, the inventive heteroindane analogs described herein can be used in the treatment of, for example, marijuana abuse, obesity, stress, vomiting, thymic disorders, dyskinesia, anxiety disorders, psychotic disorders, cognitive disorders, mood disorders, delirious disorders, psychosomatic-induced disease, epilepsy, glaucoma, nausea associated with cancer chemotherapy and AIDS wasting syndrome and other ailments in which cannabinoid system is implicated as well as for treatment of alcohol, opioid, nicotine and cocaine addiction, etc While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. A compound of formula I below, and physiologically acceptable salts:

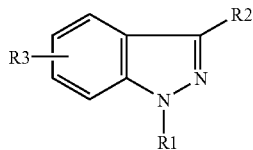

wherein,

R1 is -Q-Z;

Q is an optionally present alkyl group having 1 to about 7 carbon atoms if present;

Z is, in any possible position, any possible member selected from 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; or any above group substituted on at least one available ring carbon atom by an alkyl group and independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; and wherein the connecting point to the Z group can be any possible ring atom; or Z is, in any possible position, any possible member selected from a heterocyclic ring having about 4 to about 7 ring members, a heteroaromatic ring having about 5 to about 7 ring members, a heterobicyclic ring, a heterotricyclic ring, a heteropolycyclic ring; or any above group comprising a substituent group on at least one available ring atom; and wherein the connecting point to the Z group can be any possible ring atom; or Z is, in any possible position, any possible member selected from

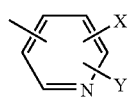 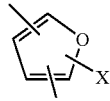 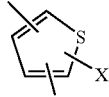

-continued

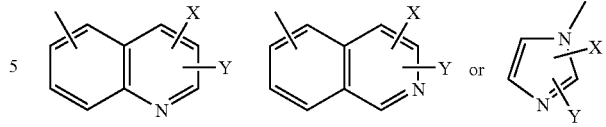

or any of the above groups with a substituent group on at least one available ring atom and the connecting point to the Z group can be any possible ring atom, wherein X and Y in the Z structure each independently selected from H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1, X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms, $X_1$ and $X_2$ are each independently selected from H or alkyl, or $X_1$ and $X_2$ together are part of a heterocyclic ring having about 4 to about 7 ring members and optionally one additional heteroatom selected from O, N or S, or $X_1$ and $X_2$ together are part of an imide ring having about 5 to about 6 members, $X_3$ is selected from H, alkyl, hydroxyloweralkyl or alkyl-$NX_1X_2$;

R2 is X-Z;

X is selected from C(O), C(O)O, OC(O)O, NC(O)O, C(O)NT, NTC(O), OC(O)NT, C(O)NTT, C(O)NTNT, NTC(O)NT, T is selected from H, an alkyl group consisting of 1 to about 4 C atoms, a heteroalkyl group consisting of 1 to about 4 C atoms, a carbocyclic ring having about 4 to about 7 ring members, or any above group having a substituent group on at least one available ring atom; wherein the variable T can not be substituted with a heteroaryl, heteroaromatic, or heterocyclic group;

Z is, in any possible position, any possible member selected from an adamantyl group, a tricyclic ring, a polycyclic ring; piperidine,

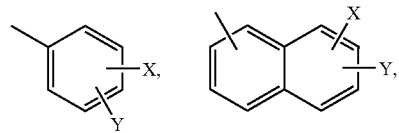

or any above group consisting of a substituent group on at least one available ring atom; and wherein the connecting point to the Z group can be any possible ring atom;

wherein X and Y in the Z structure are each independently selected from H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms, and the variable X and Y, is not and can not be substituted with a heteroaryl, heteroaromatic, or heterocyclic; and R3 is a substituent at any or all of the possible 4-, 5-, 6- and/or 7-positions, wherein each substituent is independently selected from H, halogen, $N_3$, NCS, CN, $NO_2$, $NX_1X_2$, $OX_3$, OAc, NHCOalkyl, CHO, $CF_3$, $COOX_3$, $SO_3H$, $SO_2NX_1X_2$, $CONH_2$, acyl, substituted acyl, aroyl, substituted aroyl, O-acyl, O-aroyl, OalkylOH, $OalkylNX_1X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms, $X_1$ and $X_2$ are each independently selected from H or alkyl, or $X_3$ is selected from H, alkyl, hydroxyloweralkyl or alkyl-$NX_1X_2$;

wherein $R_3$ does not represent and is not substituted with a heteroaryl, heteroaromatic or heterocyclic ring.

2. The compound of claim 1 wherein R1 is -Q-Z; Q is an optionally present alkyl group having 1 to about 7 carbon atoms if present; and Z is heteroadamantyl.

3. The compound of claim 1 wherein R2 is X-Z; and Z is adamantyl.

4. A pharmaceutical composition comprising at least one member selected from an excipient, a vehicle, an adjuvant, a flavoring, a colorant, or a preservative and a therapeutically effective amount of at least one substantially separated and purified compound selected from claim 1 or a physiologically acceptable salt thereof.

5. A method of stimulating a cannabinoid receptor in an individual or animal comprising administering to the individual or animal a pharmaceutical composition including a therapeutically effective amount of at least one substantially separated and purified compound selected from claim 1 or a physiologically acceptable salt thereof.

6. A method of selectively stimulating CB2 cannabinoid receptors in an individual or animal comprising administering to the individual or animal a pharmaceutical composition including a therapeutically effective amount of at least one substantially separated and purified compound selected from claim 1 or a physiologically acceptable salt thereof.

7. A method of treating a condition selected from central pain, peripheral pain, inflammatory pain, neuropathy, a neurodegenerative disease selected from mutiple sclerosis, Amyotrophic lateral sclerosis, Parkison's disease, Huntington's chorea, or Alzhemier's disease, inflammation, pain associated with cancer chemotherapy: comprising administering to an individual or animal in need of treatment a pharmaceutical composition including a therapeutically effective amount of at least one substantially separated and purified compound selected from claim 1 or a physiologically acceptable salt thereof.

8. The compound of claim 1 wherein R1 is -Q-Z; Q is an optionally present alkyl group having 1 to about 7 carbon atoms if present; and Z is in any possible position, any possible member selected from, 1-, 2-, 3- or 4-piperidinyl, 2-, 3- or 4-morpholinyl,; or any above group substituted on at least one available ring atom by an alkyl group; or any above group independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; or any above group substituted on at least one available ring carbon atom by an alkyl group and independently substituted on at least one available ring nitrogen atom by at least one of an alkyl group, a benzyl group, a lower-alkoxybenzyl group, a benzhydryl group, a substituted benzhydryl group, a phenyl group, a substituted phenyl group, a methylbenzyl group, a substituted methylbenzyl group; and wherein the connecting point to the Z group can be any possible ring atom.

9. The compound of claim 1 wherein R1 is -Q-Z; Q is an optionally present alkyl group having 1 to about 7 carbon atoms if present; and Z is in any possible position, any possible member selected from

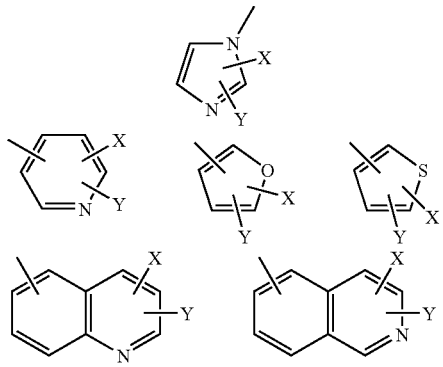

and or any above group consisting of a substituent group on at least one available ring atom; and wherein the connecting point to the Z group can be any possible ring atom wherein X and Y in the Z structure each independently selected from H, halogen, $N_3$, NCS, CN, $NO_2$, $NX_1X_2$, $OX_3$, OAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms, $X_1$ and $X_2$ are each independently selected from H or alkyl, or $X_1$ and $X_2$ together are part of a heterocyclic ring having about 4 to about 7 ring members and optionally one additional heteroatom selected from O, N or S, or $X_1$ and $X_2$ together are part of an imide ring having about 5 to about 6 members, $X_3$ is selected from H, alkyl, hydroxyloweralkyl or alkyl-$NX_1X_2$.

10. The compound of claim 1 wherein R1 is -Q-Z; Q is an alkyl group having 1 to about 7 carbon atoms; and Z is imidazole.

11. The compound of claim 1 wherein R1 is —$(CH_2)_{1-7}$- imidazole.

12. The compound of claim 1 wherein R2 is X-Z; X is selected from C(O) or C(O)NH and Z is in any possible position, any possible member selected from an adamantyl group, a tricyclic ring, a polycyclic ring; or any above group consisting of a substituent group on at least one available ring atom, and the connecting point to the Z group can be any possible ring atom.

13. The compound of claim 1 wherein R2 is X-Z; X is selected from C(O) or C(O)NH and Z is piperidine,

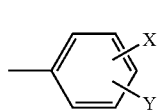 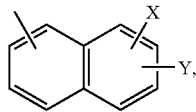

or any above group having a substituent group on at least one available ring atom; and wherein the connecting point to the Z group can be any possible ring atom;

wherein X and Y in the Z structure are each independently selected from H, halogen, $N_3$, NOS, CN, $NO_2$, $NX_1X_2$, $OX_3$, QAc, NHCOalkyl, CHO, $CF_3$, $C(O)OX_3$, $SO_3H$, $SO_2NX_1X_2$, $CONX_1X_2$, acyl, substituted acyl, aroyl, substituted aroyl, heteroaroyl, substituted heteroaroyl, O-acyl, O-aroyl, OalkylOH, $OalkylNX_1X_2$, NH-acyl, NH-aroyl, alkoxy, alkylmercapto, alkylamino or di-alkylamino, alkylsulfinyl, alkylsulfonyl or methylene dioxy when Z comprises a structure having two adjacent carbon atoms, and the variable X and Y, is not and can not be substituted with a heteroaryl, heteroaromatic, or heterocyclic group.

14. The compound of claim 1 wherein R2 is X-Z; X is C(O)NH and Z is adamantyl.

15. The compound of claim 1 wherein each R3 is selected from H, CN, $NH_2$ or halogen.

16. The compound of claim 1 wherein each R3 is selected from H or halogen.

17. The compound of claim 1 in substantially purified form.

18. The method of claim 5 wherein the pharmaceutical composition comprises at least one member selected from an excipient, a vehicle, an adjuvant, a flavoring, a colorant, or a preservative.

19. The method of claim 7 wherein the condition is selected from central pain, peripheral pain, inflammatory pain, inflammation, and pain associated with cancer chemotherapy.

20. The method of claim 7 wherein the condition is selected from central pain, peripheral pain, inflammatory pain and inflammation.

21. The method of claim 7 wherein the condition is selected from central pain, peripheral pain, inflammatory pain and inflammation; the pharmaceutical composition comprises at least one member selected from an excipient, a vehicle, an adjuvant, a flavoring, a colorant, or a preservative; and the compound is in substantially purified form.

* * * * *

UNITED STATES PATENT AND TRADEMARK OFFICE
CERTIFICATE OF CORRECTION

PATENT NO. : 7,666,867 B2
APPLICATION NO. : 10/493093
DATED : February 23, 2010
INVENTOR(S) : Makriyannis et al.

It is certified that error appears in the above-identified patent and that said Letters Patent is hereby corrected as shown below:

Column 24:
Line 18, delete "OalkylNX$_1$, X$_2$," and substitute --OalkylNX$_1$X$_2$,--.

Column 27:
Line 16, delete "NOS" and substitute --NCS--.

Line 17, delete "QAc" and substitute --OAc--.

Signed and Sealed this

Eighteenth Day of May, 2010

David J. Kappos
*Director of the United States Patent and Trademark Office*